US006269266B1

(12) United States Patent
Leysieffer

(10) Patent No.: US 6,269,266 B1
(45) Date of Patent: Jul. 31, 2001

(54) POWER SUPPLY MODULE FOR AN IMPLANTABLE DEVICE

(75) Inventor: Hans Leysieffer, Taufkirchen (DE)

(73) Assignee: Implex Aktiengesellschaft Hearing Technology, Ismaning (DE)

( * ) Notice: Subject to any disclaimer, the term of this patent is extended or adjusted under 35 U.S.C. 154(b) by 0 days.

(21) Appl. No.: 09/359,050

(22) Filed: Jul. 23, 1999

(30) Foreign Application Priority Data

Aug. 20, 1998 (DE) ........................................ 198 37 912

(51) Int. Cl.[7] ........................................ A61N 1/00

(52) U.S. Cl. ........................................ 607/2

(58) Field of Search ........................................ 429/59, 51, 61, 429/62, 53, 57, 66; 607/2, 33, 29

(56) References Cited

U.S. PATENT DOCUMENTS

| | | |
|---|---|---|
| 3,824,129 | 7/1974 | Fagan, Jr. . |
| 4,082,097 | 4/1978 | Mann et al. . |
| 4,275,739 | 6/1981 | Fischell . |
| 5,279,292 | 1/1994 | Baumann et al. . |
| 5,314,451 | 5/1994 | Mulier . |
| 5,411,537 | 5/1995 | Munshi et al. . |
| 5,755,743 | 5/1998 | Volz et al. . |

FOREIGN PATENT DOCUMENTS

| | | |
|---|---|---|
| 33 31 620 | 3/1984 | (DE) . |
| 0 322 112 | 6/1989 | (EP) . |
| 0 360 395 | 3/1990 | (EP) . |
| 0 364 995 | 4/1990 | (EP) . |
| 0 370 634 | 5/1990 | (EP) . |
| 0 470 726 | 2/1992 | (EP) . |
| 0 573 998 | 12/1993 | (EP) . |
| 0 674 351 | 9/1995 | (EP) . |
| 0 739 047 | 10/1996 | (EP) . |

*Primary Examiner*—Scott M. Getzow
(74) *Attorney, Agent, or Firm*—Nixon Peabody LLP; David S. Safran

(57) ABSTRACT

A power supply module (58) for an implantable device (54) has a biocompatible outer housing (80) which holds a repeatedly rechargeable electrochemical battery (90) that supplies electrical power to a main module (56) of the implantable device (54) via a coupling element (82). The outer housing is made as a hermetically tight protective housing or holds such a housing (88). The protective housing (88) has a detector element (92) which is designed or adjustable to actuate at least one switching element (94) which prevents recharging and/or discharging of the battery (90) when the battery is in an unallowable operating state. The coupling element (82) is preferably made detachable.

39 Claims, 7 Drawing Sheets

POWER SUPPLY MODULE FOR AN IMPLANTABLE DEVICE

BACKGROUND OF THE INVENTION

1. Field of the Invention

The invention relates to a power supply module for an implantable device, the power supply module encompassing a biocompatible outer housing which holds a repeatedly rechargeable electrochemical battery that supplies electrical power to the main module of the implantable device via a coupling element.

2. Description of Related Art

U.S. Pat. No. 5,279,292 discloses an implantable device which is a hearing aid or a tinnitus masker which has, in one embodiment, a main module and a power supply module. The two modules are each accommodated in a separate biocompatible housing, power transmission from the power supply module to the main module taking place via a coupling element with a metallic or metallically separated and inductively coupled connection. The housing of the power supply module can hold a battery, charging electronics and a receiving resonant circuit which can be inductively coupled to a transmitting resonant circuit of a charging means which can be attached outside the body. One important advantage of the modular structure is that, with the implantation site of the power supply module, the individual is not linked to that of the main module. Rather the power supply module can be implanted anywhere on the body where there is enough space, in addition a battery with relatively large electrical capacitance can be used. This applies to a coupling element which is made for a permanent connection in the same way as for a detachable coupling element. The latter, at the same time, allows replacement of the battery without the need to replace the entire system.

The coupling element which is disclosed in U.S. Pat. No. 5,279,292 and which is made for a metallically separated and inductively coupled detachable connection comprises two coupling coils and a ferrite rod as the common core. One coupling coil is assigned to the power supply module and is supplied as part of a serial tuned circuit from the battery via an oscillator, the second coupling coil, which acts as the receiving coil, is connected to the main module via a flexible connecting lead. The AC voltage induced in the receiving coil is available via a rectifier to operate the hearing aid.

German patent disclosure document DE3 31 620 A1 describes a hermetically tight, plug-and-socket connection which is used for a detachable metallic connection of the electrode feed lines to an implantable pacemaker, a defibrillator or a cardioverter.

U.S. Pat. No. 5,755,743 relates to a contact arrangement for a detachable electrical connection between an implant housing and other, especially sensor and actuator components, with which a high degree of miniaturization can be achieved.

One special problem in the use of repeatedly rechargeable electrochemical batteries is that, in case of excess charging or a short circuit between the terminal contacts or poles of the battery, a pressure rise within the battery housing can occur which leads to its deformation which, in turn, can become so great that chemicals, especially in gaseous form, emerge.

Published European Patent Application 0 322 112 (corresponding to U.S. Pat. No. 4,756,983), published European Patent Application 0 360 395 (corresponding to U.S. Pat. No. 4,937,153) and published European Patent Application 0 370 634 (corresponding to U.S. Pat. No. 4,871,553) disclose providing electrochemical batteries with a switching element which, when a certain tolerated boundary deformation of the battery housing is exceeded, preferably, irreversibly breaks an electrical terminal contact away from the pertinent electrochemically active electrode in order to prevent further deformation of the battery housing. The battery housing comprises an electrically conductive cylindrical housing segment closed on the face, and in contact with an electrode, and on the face, the plate-shaped switching element being attached centrally by means of an electrically insulating cement from the outside. The electrically conductive switching element, in its base position, forms above its outside edge an electrical connection between the housing segment and the electrical terminal contact which projects to the outside and which is located in the center of the switching element. When the pressure rises within the battery housing, the face of the housing segment which acts as a detector element arches to the outside, causing contact to be interrupted between the housing segment and the outside edge of the switching element, and thus, between the electrode and the terminal contact. Typical applications of these switching elements are type "D" standard batteries. The curvature of the face, starting from which the switching element breaks the electrical contact, in this case, is 0.76 mm to 1.8 mm. For a curvature of more than 1.8 mm, leakage of chemicals from within the battery can usually be expected.

Published European Patent Application 0 470 726 discloses an electrochemical battery with a cylindrical battery housing and a pressure membrane as the detector element which is integrated on the face in the battery housing and which curves when the pressure rises within the battery housing, by which a plate-shaped switching element, which is connected to the pressure membrane in the center, reversibly or irreversibly interrupts the electrical contact between an electrode and a terminal contact of the battery.

Published European Patent Application 0 674 351 (corresponding to U.S. Pat. No. 5,585,207) discloses an electrochemical battery with a battery housing which comprises a cutting device which can be actuated by a pressure membrane and which irreversibly breaks an electrical conductor which connects the terminal contact of the battery with an electrochemically active electrode when a boundary pressure within the battery housing is exceeded.

When a switching element is being used which breaks the electrical connection between a terminal contact and the associated electrochemically active electrode when a certain pressure within the battery housing is exceeded, it is possible for the pressure to continue to increase and ultimately for chemicals to discharge from the battery housing or even for it to explode. For this reason, it was proposed (for example, in Published European Patent Applications Nos. 0 364 995, 0 573 998 or 0 739 047, which correspond to U.S. Pat. Nos. 4,943,497, 5,418,082 and 5,766,790, respectively) that a pressure membrane which actuates the switching element and which is located in the battery housing be provided with a bursting area via which after activation of the switching element and a further pressure increase chemicals can emerge from within the battery housing.

The safety measures cited in the aforementioned prior art for electrochemical batteries are not adequate or are unsuited for use in a power supply module of implantable devices, since for this purpose, especially high demands, particularly with respect to safety and reliability, must be satisfied with, at the same time, a reduction of all dimensions to the largest degree possible.

SUMMARY OF THE INVENTION

Thus, a primary object of the present invention is to devise a power supply module for an implantable device which precludes risk to the implant wearer in case of battery malfunction, for example, by contamination with toxic substances, and which satisfies the specific requirements for implantable devices.

This object is achieved, in accordance with the invention, by the provision of a power supply module having a biocompatible outer housing which holds a repeatedly rechargeable electrochemical battery which supplies electrical power to a main module of the implantable device via a coupling element, and in which the outer housing is made as a hermetically sealed protective housing, or holds such a housing, and in which the protective housing has a detector element which for actuating at least one switching element which prevents recharging and/or discharging of the battery when the battery is in an unallowable operating state.

Basically, the implantable device can be any implantable medical or biological device, and thus, among others, can be an active electronic hearing implant, cardiac pacemaker, defibrillator, drug dispenser, nerve or bone growth stimulator, neurostimulator, pain suppression device or the like.

By the outer housing being made as a hermetically sealed protective housing or holding such a housing, the battery is always held hermetically sealed in the housing and it is possible to use a conventional battery, for example, a ordinary button cell, without special regard to the material selection or the like. Chemicals leaking from within the battery housing are reliably retained in the hermetically sealed protective housing which, moreover, can be made explosion-proof.

If the biocompatible outer housing accommodates a hermetically sealed protective housing which, for its part, surrounds the battery, the protective housing itself need not be made biocompatible, so that there is greater freedom in the choice and optimization of material.

Here, hermetically sealed is defined, preferably, as hermetic gas-tightness as per Mil-Std 883 D. This design ensures that, when using a hermetically sealed protective housing which, itself, is housed, in turn, in a hermetically sealed, and furthermore, biocompatible outer housing, besides toxic liquids, no gases can escape from the protective housing. These battery gases occur, basically, in small amounts even in regular normal operation of a battery surrounded by the protective housing. The hermetic gas-tightness of the protective housing reliably prevents risk to the electronics accommodated in the outer housing, outside the protective housing; this means that the electronic circuits, especially integrated circuits, can remain unprotected since contamination by even the smallest amounts of escaping battery gases is not possible.

An unallowable operating state of the battery, which can be the continuous escape of chemicals from the battery housing in addition to its expansion, which leads to a pressure rise in the protective housing or in the outer housing made as the protective housing, is answered by the detector element, preferably with a change in shape, which directly causes mechanical actuation and/or electrical actuation, via evaluation electronics, at least one switching element which prevents further recharging and/or discharging of the battery.

The at least one switching element can be designed to be fundamentally reversible or irreversible and can be accommodated or integrated in the outer or protective housing. Furthermore, it is possible for the at least one switching element to be placed in the housing of the main module. The switching element can be made as a break contact which electrically interrupts a recharging and/or discharging current in an unallowable operating state of the battery. Recharging and/or discharging of the battery can, furthermore, be prevented by the switching element being made as a make contact which electrically short circuits the battery when it is in an unallowable operating state in order to discharge it in a controlled manner. Alternatively, the make contact can electrically short circuit a recharging circuit in order to interrupt further power supply to the battery.

Detector and switching elements which are suitable for use in this invention are described in commonly-owned, U.S. Pat. No. 6,143,440 claiming priority of German Patent Application No. 198 37 909.9 file Aug. 20, 1998.

The coupling element for transmission of electrical power can, as already mentioned, be made either permanent or detachable, and can enable a metallic, or alternatively, a metallically separated and inductive connection. A permanent connection provides especially high reliability but the detachable, metallically separated and inductive connection has the advantage that there is no metallic connection between the power supply module and the main module which need be sealed to prevent the penetration of body fluids. DC-less power transmission, whether using the detachable or permanent metallic or metallically separated connection, generally reduces the risk that ion migration takes place over a longer time in the same direction in an insulator between locations of different electrical voltage; after some time, this increases the electrical conductivity of the insulator and leads to leakage currents.

The combination of main module and power supply module can be made especially compact when one half of the coupling element assigned to the power supply module is integrated in the outer or the protective housing and the complementary half of the coupling element assigned to the main module is integrated in the housing of the main module.

Greater freedom in placement of the power supply module occurs when the half of the coupling element assigned to the power supply module is electrically connected to the power supply module via a flexible connecting lead. In addition or alternatively, also, one half of the coupling element assigned to the main module can be electrically connected to the main module via a flexible connecting lead.

When the outer or protective housing of the power supply module accommodates charging/discharging electronics for control of recharging and/or discharging of the battery and when the coupling element is detachable, when the power supply module is replaced by one of a different battery type, the charging/discharging electronics can be changed at the same time and matched to the respective battery type. However, the charging/discharging electronics can also be accommodated in the housing of the main module.

In another advantageous embodiment of the invention, there is a charging current feed arrangement into which power can be supplied via a charging device located outside of the body, and separated from the power supply module and main module. The power can be transferred by electrical, magnetic and electromagnetic fields into the charging current feed arrangement. One suitable version of a charging current feed arrangement with a receiving coil and a charging device with an inductively coupled transmitting coil is shown in the already mentioned U.S. Pat. No. 5,279,292.

The charging current feed arrangement can be accommodated in the outer or protective housing of the power supply module or alternatively in the housing of the main module.

In the conventional manner (for example, as described in U.S. Pat. No. 4,991,582), the housing which holds the charging current feed arrangement can be made at least in part of ceramic and can be provided with a metal housing part in order to achieve greater transparency to electrical, magnetic and electromagnetic fields as compared to a purely metallic housing. Biocompatible metallic materials include titanium, titanium alloys, niobium, niobium alloys, tantalum or implantable steels. Suitable biocompatible ceramics include aluminum oxide and boron nitride.

The cost of manufacturing the housing can be greatly reduced when the charging current feed arrangement comprises at least one coil of biocompatible metal which is surrounded by a biocompatible polymer and which is fixed to an outer side of the housing of the main module, or alternatively, to the outer or protective housing. The coil, which is made, for example, of pure gold, gold alloys, platinum, platinum-iridium, niobium, tantalum or other metallic materials which are biocompatible and resistant to body fluids, can be supplied with power with high efficiency without a production-intensive metal ceramic composite housing being necessary for this purpose. The same applies to optionally provided power emission by a coil to be used as a transmission coil or an additional transmission coil which is surrounded, likewise, by a biocompatible polymer, with which, for example, information of a bidirectional telemetry circuit on the relative position of the coil of the power supply module relative to the transmission coil of the charging device and/or on the charging state of the battery can be transcutaneously exchanged. The implanted part of the telemetry circuit can be integrated both in the main and also in the power supply module.

The biocompatible polymer, preferably silicone, polytetrafluorethylene (PTFE), polymethane, parylene, or the like, on the one hand, can be used to increase the mechanical cohesion of the coil itself, and on the other hand, for mechanical linkage of the coil to the corresponding housing.

If the coil of the charging current feed arrangement is placed in the direction of the largest dimension of the main module or the outer or protective housing laterally next to the latter, and a straight line which runs in this direction forms an angle in the range from 5° to 25° with respect to a perpendicular to the coil axis, a unit is formed which is comprised of the coil and the corresponding housing, which is especially well suited for implantation on the outside of the human skull, especially in the area of the mastoid plane, as is the case, for example, in at least partially implantable hearing aids, tinnitus maskers or retina stimulators, and was already described in the commonly owned, co-pending application U.S. Pat. No. 6,143,440 claiming priority based upon German patent application 198 29 637 1.

If the coil on the main module or on the outer or protective housing is flexibly fixed, especially by means of the biocompatible polymer, the unit comprised of the coil and housing can be especially well adapted geometrically to the implantation site.

In another advantageous embodiment of the invention, at least one switching element is designed to be mechanically actuated by the detector element in an unallowable operating state of the battery and is integrated in the outer or protective housing. The switching element is thus actuated without nonmechanical intermediate elements and works very reliably. The detector element can be made as a deflectable membrane and can be part of the protective housing. For example, an outside wall or partition of the hermetically sealed protective housing can be made at least partially as a detector element; this allows a space-saving construction and easily predictable change of shape of the detector element in an unallowable operating state of the battery, for example, due to a pressure rise in the protective housing.

Especially when two or more switching elements are redundantly present, at least one switching element can be electrically actuated by evaluation electronics which monitor the detector element. The evaluation electronics can, for example, detect a change in the shape of the detector element which is impressed on the latter in an unallowable operating state of the battery. Advantageously, an electrical extensometer is used which picks up the change in shape of the detector element and responds with a change of an electrical quantity which is monitored by the evaluation electronics. If the electrical extensometer is a passive system, it can convert the change in the shape of the detector element into a change of its electrical resistance (strain gauge), its inductance, or its capacitance. Alternatively, an active electrical extensometer can be used which reacts like, for example, a piezoelement, with a change in charge due to a change in shape applied by the detector element to the extensometer.

The evaluation electronics can be accommodated in the outer or protective housing. Alternatively, the main module can also include the evaluation electronics. In the latter case, the coupling element and an optionally present flexible connecting lead can be advantageously made such that, between the main module and the power supply module, a signal can be transmitted in addition to power.

It goes without saying that the power supply module can also supply electric power to one or more secondary modules which can be connected to the main module. Such secondary modules can be actuator and/or sensor components.

These and further objects, features and advantages of the present invention will become apparent from the following description when taken in connection with the accompanying drawings which, for purposes of illustration only, show several embodiments in accordance with the present invention.

DETAILED DESCRIPTION OF THE INVENTION

Figure 1:
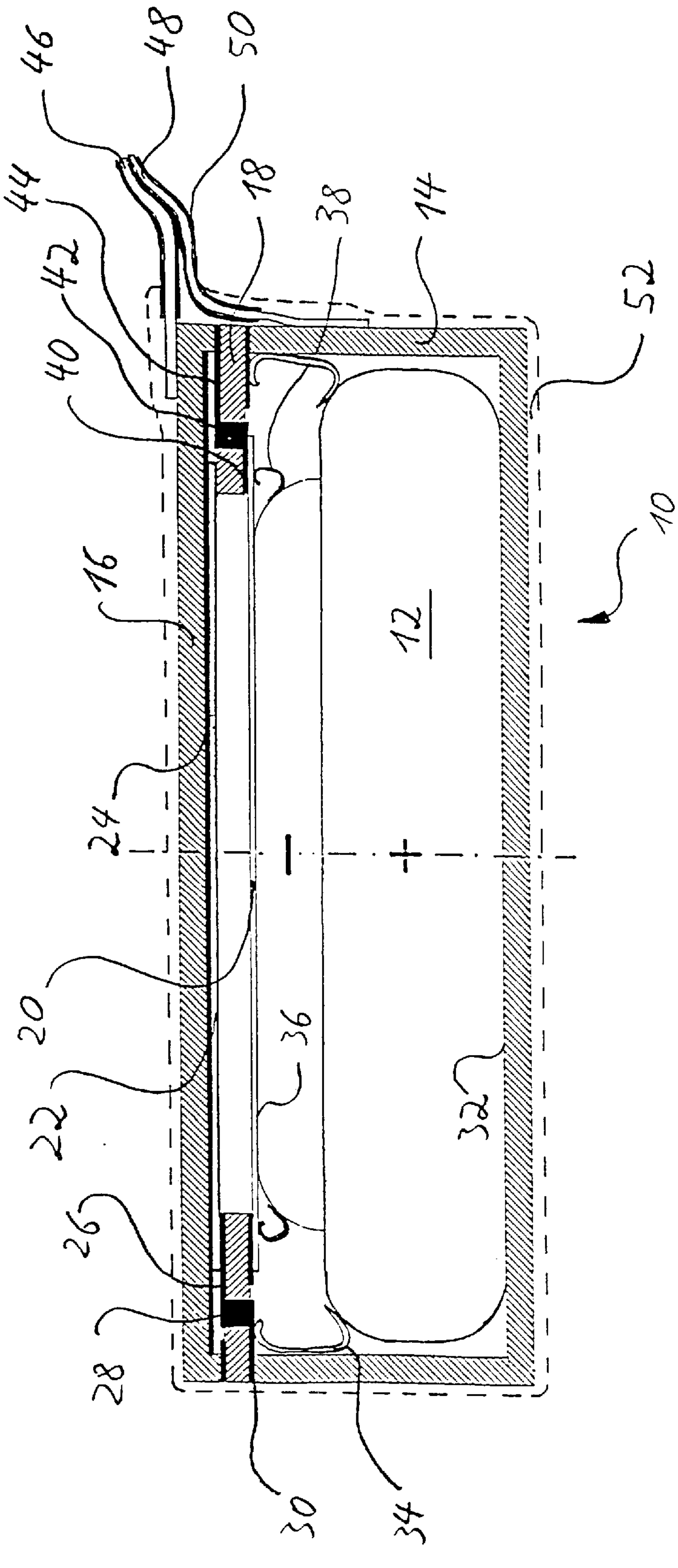
FIG. 1 is a schematic cross-sectional view of a hermetically sealed, biocompatible protective housing with a repeatedly rechargeable electrochemical battery, a detector and a switching element.

FIG. 1 shows a protective housing 10 for a repeatedly rechargeable electrochemical battery 12 which is a conventional button cell. The protective housing 10 has a one-piece bottom 14 of electrically conductive material and is sealed by a, likewise, electrically conductive cover 16, an insulating ring 18 of oxide ceramic being soldered between the cover 16 and the bottom 14. The insulating ring 18 has an inner diameter which is less than that of the cylindrical side wall of the bottom 14. The bottom of the insulating ring 18 bears, in an electrically insulated manner on a membrane 20 and its top bears in the same manner on a contact membrane 22. The two membranes 20 and 22 are made of electrically conductive material, the top of the contact membrane 22 being electrically insulated relative to the adjacent cover 16 by means of an insulating layer 24 and being placed at the electrical potential of the bottom 14 via a metal coating 26, a through-plated hole 28 and a solder layer 30. The battery 12 is hermetically sealed by the surrounding bottom 14, insulating ring 18 and membrane 20, and its positive pole (the battery poles are labelled + and – in FIG. 1), via a face 32, makes contact with the inner base surface of the bottom 14. A spring 34 is located between a shoulder of the battery 12 and the transition area between the insulating ring 18 and the side wall of the bottom 14. Spring 34 is used for centering and play-free contact of the face 32 of the battery 12 with the base surface of the bottom 14. At the same time, the spring 34 is in electrical contact with the side wall of the base 14, the solder layer 30 and the positive pole of the battery 12 which extends into the area of the shoulder adjoining the spring 34.

The negative pole of the battery 12 makes contact with the bottom of the membrane 20 via a face 36 of the battery 12 and via an optional spring 38. A metal coating 40 on the bottom of the insulating ring 18, a through-plated hole 42 through the insulating ring and a solder layer 44 close the electrical connection between the membrane 20 and the cover 16 from which the negative pole of the battery 12 is tapped via a terminal 46. A terminal 48 on the outer side wall of the bottom 14 is used to tap the positive pole of the battery 12. The two terminals 46, 48 are surrounded by a biocompatible insulating jacket 50; a biocompatible polymer 52, such as silicone, jackets the protective housing 10 and the housing-side ends of the terminals 46, 48.

Therefore, while the membrane 20 is connected to the negative pole of the battery 12, the contact membrane 22 is located at a distance from the membrane 20 which corresponds to the thickness of the insulating ring 18 and is electrically connected with the positive pole of the battery 12. This distance is such that, in an unallowable operating state of the battery 12, especially when the volume of the battery 12 expands and/or when battery gases escape, which leads to a pressure rise within the protective housing 10, a curvature is impressed on the membrane 20, which functions as a detector element, which is sufficient to make electrically conductive contact with the contact membrane 22 so that battery 12 is electrically short circuited.

A section of the solder connection 44 can be dimensioned as a fusible link which burns through irreversibly if a recharging or discharging current exceeds a given threshold value without the contact membrane 22 making contact with the membrane 20. Further power supply and emission via terminals 46, 48 is thus suppressed.

In the version of the protective housing as shown in FIG. 1, the combination of the detector membrane 20 and the contact membrane 22 is used as a reversibly operating switching element which is made as a make contact and which is mechanically activated by a detector element 20. The entire unit shown in FIG. 1 represents one embodiment of a power supply module with a biocompatible hermetically sealed outer housing, the outer housing being made as a protective housing and comprising a detector and a switching element.

Figure 2:
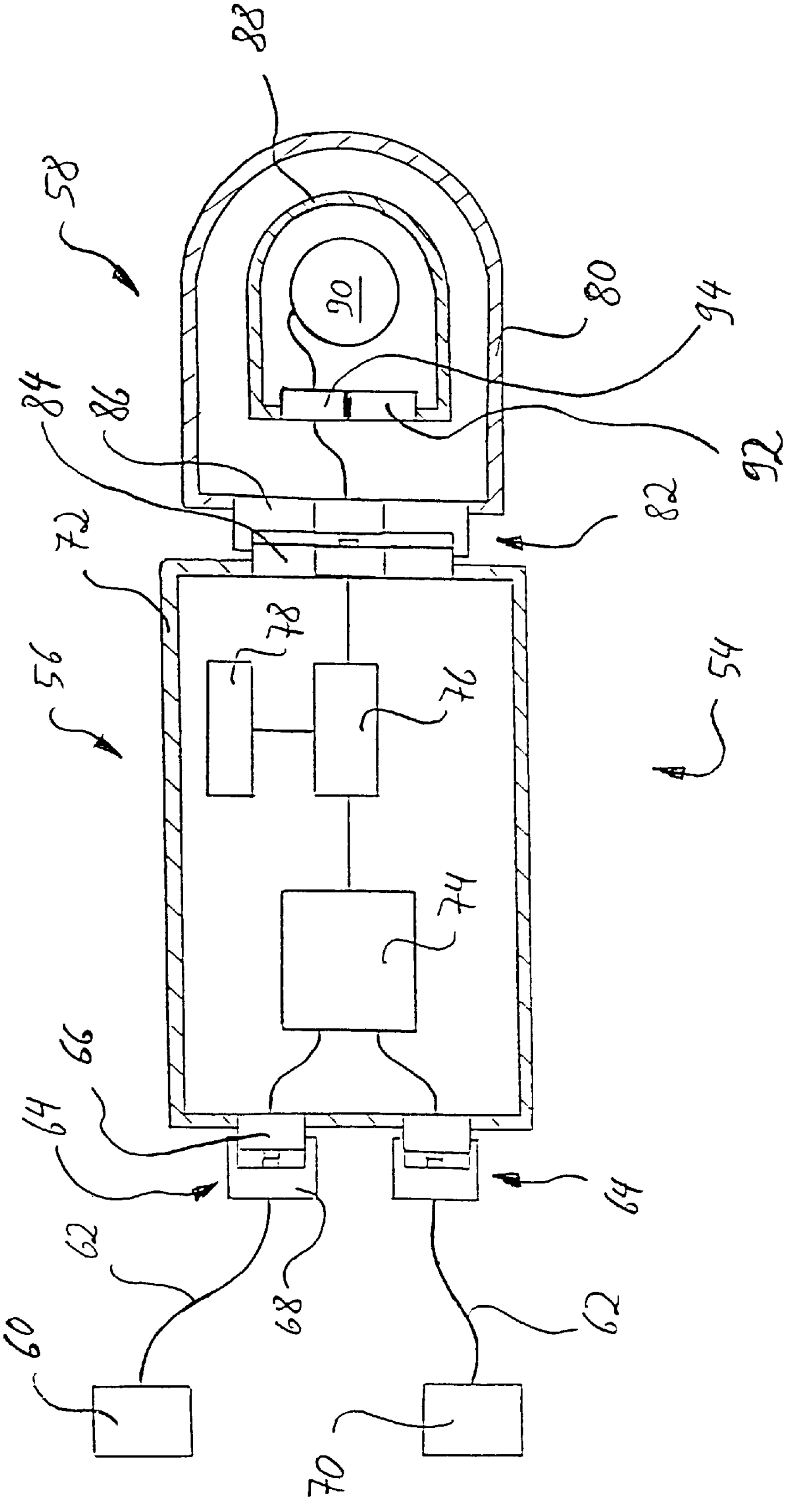
FIG. 2 is a schematic cross section of an implantable device with a main and a power supply module as well as secondary modules, the power supply module being detachably and rigidly coupled to the main module.

An implantable device 54 as shown in FIG. 2 comprises a main module 56, a power supply module 58, and secondary modules comprised of a sensor 60 and an actuator component 70. The secondary modules 60 and 70 are each connected electrically and mechanically to the main module via a flexible connecting lead 62 and a coupling element labeled 64 as a whole. The coupling element 64 has a first half assigned to the main module 56 and a secondary module-side second half 68 which is detachably coupled to the first half 66 and into which the flexible connecting lead 62 discharges. It goes without saying that all lines shown in simplified form by a single line, depending on the components which connect them, can in principle be made with one or more poles. The corresponding applies to coupling elements and line penetrations through the housings or housing parts.

The main module housing 72 of the main module 56 holds signal processing electronics 74, charging/discharging electronics 76 and a charging current feed arrangement 78 with a coil. Furthermore, the housing 72 is hermetically sealed and is made of a biocompatible material which allows sufficient permeation of the coil with electromagnetic fields of a transmitting coil of a charging device that is located outside of the body. The function of the signal processing electronics 74 is dependent on the type of implantable device. It controls the actuator component 70 according to a stored program depending on the signals of the sensor component 60 and is connected to the two components via the coupling elements 64 with first halves 66 integrated in a hermetically sealed manner in the main module housing 72. The charging/discharging electronics 76 forms a nodal point between the signal processing electronics 74, the charging current feed arrangement 78 and the rechargeable electrochemical battery 90 and is used for power distribution between these components.

A coupling element 82 with a first half 84 integrated in a hermetically sealed manner in the main module housing 72 and a second half 86, which hermetically seals a biocompatible outer housing 80 of the power supply module 58, provides a detachable, rigid mechanical linkage of the power supply module 58 to the main module 56. At the same time, coupling element 82 is used for detachable metallic contact between the battery 90 and the charging/discharging electronics 76 which is connected to the inner side of the first half 84, i.e., the side pointing into the interior of the main module housing 72. In the current path between the second half 86 of the coupling element 82 and the battery 90, which is held in a hermetically tight protective housing 88, there is a switching element 94 which is made as a break contact and which is fixed on the protective housing 88 and is mechanically actuated by a detector element 92, for example, a deflectable membrane in the outer wall or partition of the protective housing 88, when a change in shape is impressed on the detector element 92 in an unallowable operating state of battery 90.

Instead of the protective housing 88, it is possible to use the protective housing 10 of FIG. 1, which then need not be biocompatible, since it is located in the biocompatible outer housing 80. In this case, the switching element 94 would be a make contact which electrically shorts the battery 90 when it is in an unallowable operating state and interrupts further power supply and emission to or from the battery 90.

Figure 3:
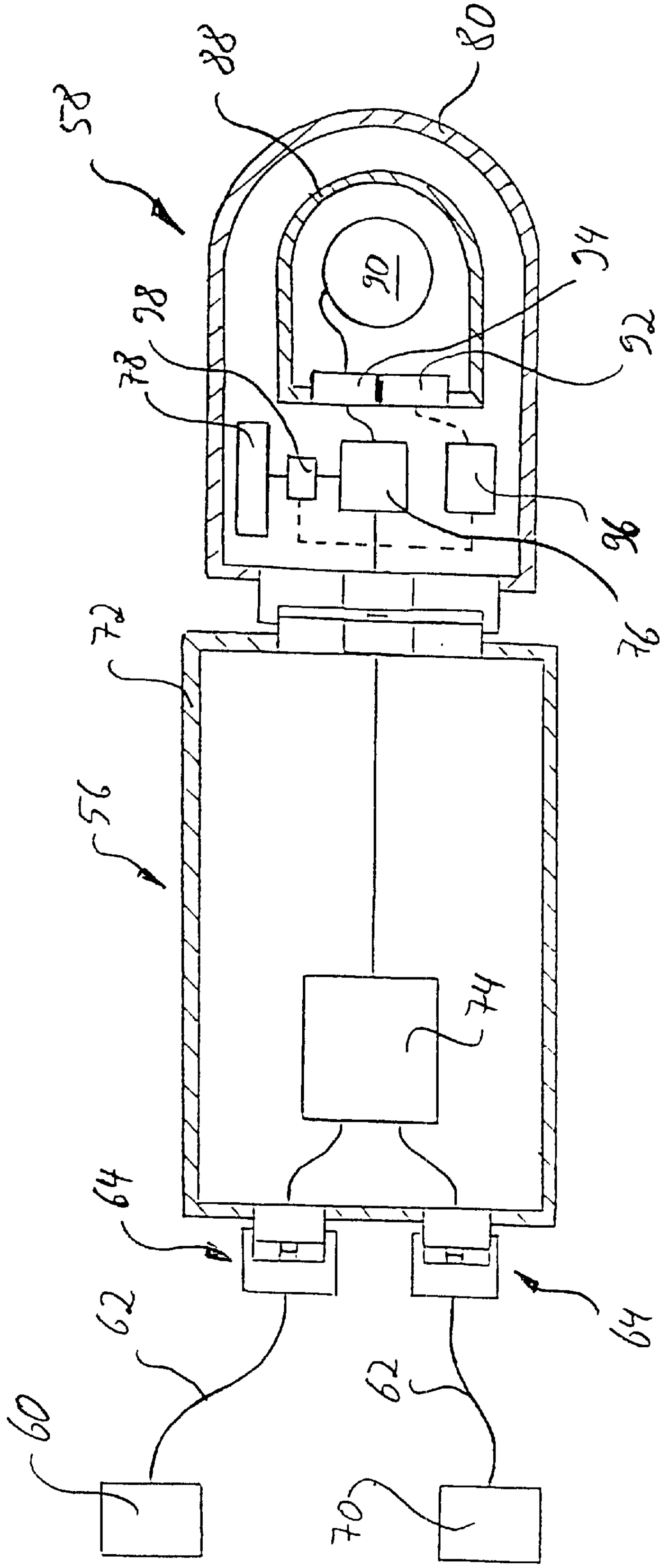
FIG. 3 is a view similar to that of FIG. 2 by showing a modified embodiment of the main and power supply module.

The embodiment of FIG. 3 differs from that of FIG. 2 essentially only in that the charging/discharging electronics 76 and the charging current feed arrangement 78 are not accommodated in the main module housing 72, but in the outer housing 80 of the power supply module 58. To increase the operating safety, evaluation electronics 96 monitor the state of the detector element 92, and depending thereon, electrically actuate a switching element 98 which is made as a break contact and which is placed in the current path between the charging current feed arrangement 78 and the charging/discharging electronics 76. The state of change in the shape of the detector element 92 is, for example, acquired via an electrical strain gauge. When a predetermined boundary shape change of the detector element 92 is exceeded, the switching element 98 interrupts further power supply from the charging current feed arrangement 78 regardless of the function of the switching element 94 so that there is redundancy.

Figure 4:
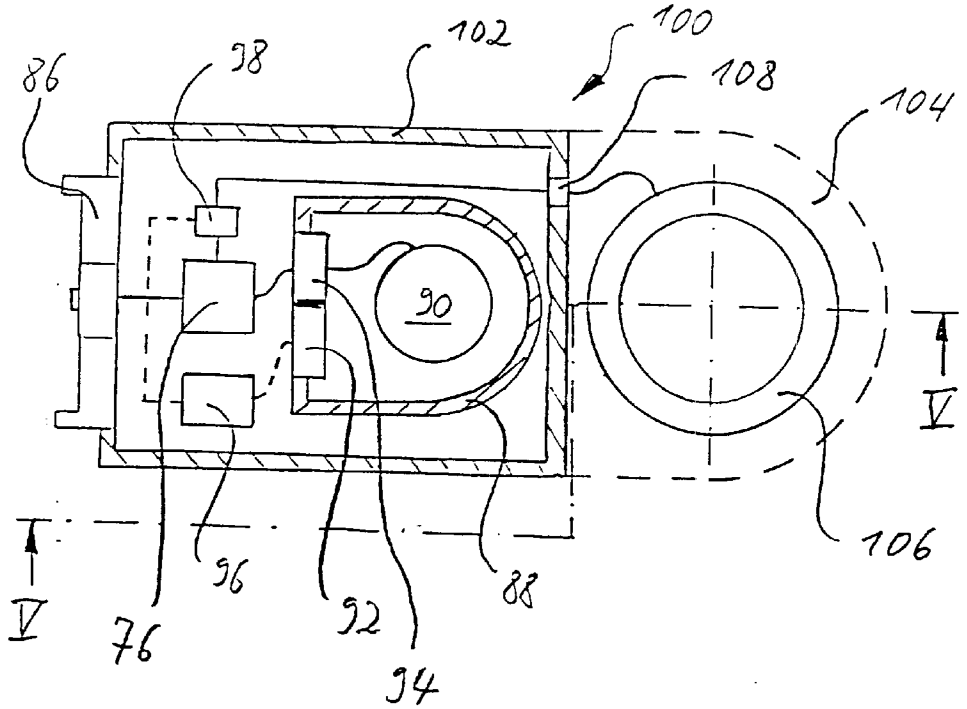
FIG. 4 is a schematic cross section of a power supply module with a coil of a charging current feed arrangement accommodated in its own housing.
Figure 5:
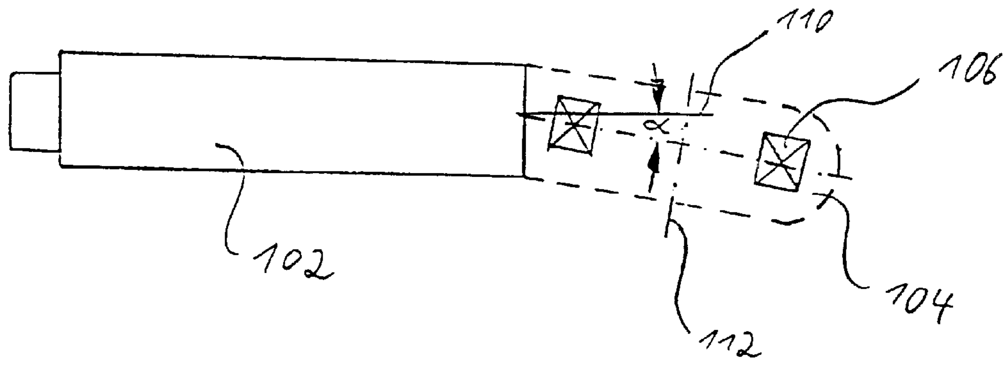
FIG. 5 a partial sectional view of the power supply module as viewed along line V—V in FIG. 4.

A power supply module 100 is illustrated in FIGS. 4 and 5 and differs from the power supply module 58 in the version of FIG. 3 mainly by placement of a coil 106 in its own housing part of biocompatible polymer 104. The coil 106 is part of the charging current feed arrangement 78 which can contain still other components which are not shown, such as for example, a capacitor for building a tuned circuit. The coil 106 which can also be several individual coils is potted with biocompatible polymer 104 which is used, at the same time, for mechanical attachment of the coil 106 to a side wall of an outer housing 102, the side wall lying perpendicular to a straight line 110 which runs in the direction of the longest extension of the outer housing 102. A straight line which runs perpendicular to the axis 112 of the coil 106 forms with the line 110 an angle $\alpha$ in the range from 5 to 25 degrees, preferably in the range from 7 to 15 degrees. The outer housing 102 integrates a hermetically tight through-hole 108 which is located in the current path between the coil 106 with the switching element 98. With respect to special versions of the through-hole 108 reference is made to the aforementioned commonly owned, U.S. Pat. No. 6,143,440, claiming priority of German Patent Application No. 198 37 909.9 file Aug. 20, 1998.

By accommodating the coil 106 outside of the outer housing 102 in a polymer jacket, the outer housing 102, except for areas in which the through-hole 108 and the second half 86 of the coupling element 82 are integrated, can be made purely metallic, especially of titanium. A metal-ceramic composite housing which is re-used to achieve a higher efficiency of power feed into the coil 106 without undue heating of the housing by eddy currents as compared to a metal housing, can be abandoned, as already mentioned in the general part of the description.

Fixing the coil 106 on the outer housing 102 by the polymer 104 can be done relatively rigidly. But, it is also possible to intentionally make the mechanical connection flexible by, for example, tapering the polymer jacketing of the coil on the side facing the outer housing 102 in the manner of tabs and only casting the tabs to the outer housing 102.

It goes without saying that, instead of angling the unit formed of the outer housing 102 and the laterally arranged coil 106, an angled coupling element 82 can be used between the main module housing 72 and the outer housing 102.

By the arrangement of the coil 106 laterally next to the outer housing 102 and jacketing with a biocompatible polymer 104, the arrangement has an especially high permeability for electrical, magnetic and electromagnetic fields in the permeation direction of the coil, i.e., essentially in the direction of the axis 112 of the coil 106. Depending on the choice of materials for the outer housing 102 and the frequency of the field used for power transmission into the coil 106, it can also be a good idea, especially to minimize the amount of space required, to place the coil on the top of the outer housing 102, and thus, in the permeation direction on the side of the outer housing 102 facing the transmission coil.

Furthermore, the coil can also be mechanically detached completely from the outer housing 102 and provided with a flexible connecting lead, and optionally, a coupling element, in order to be able to be implanted independently of the outer housing 102 at a suitable location in the body.

Figure 6:
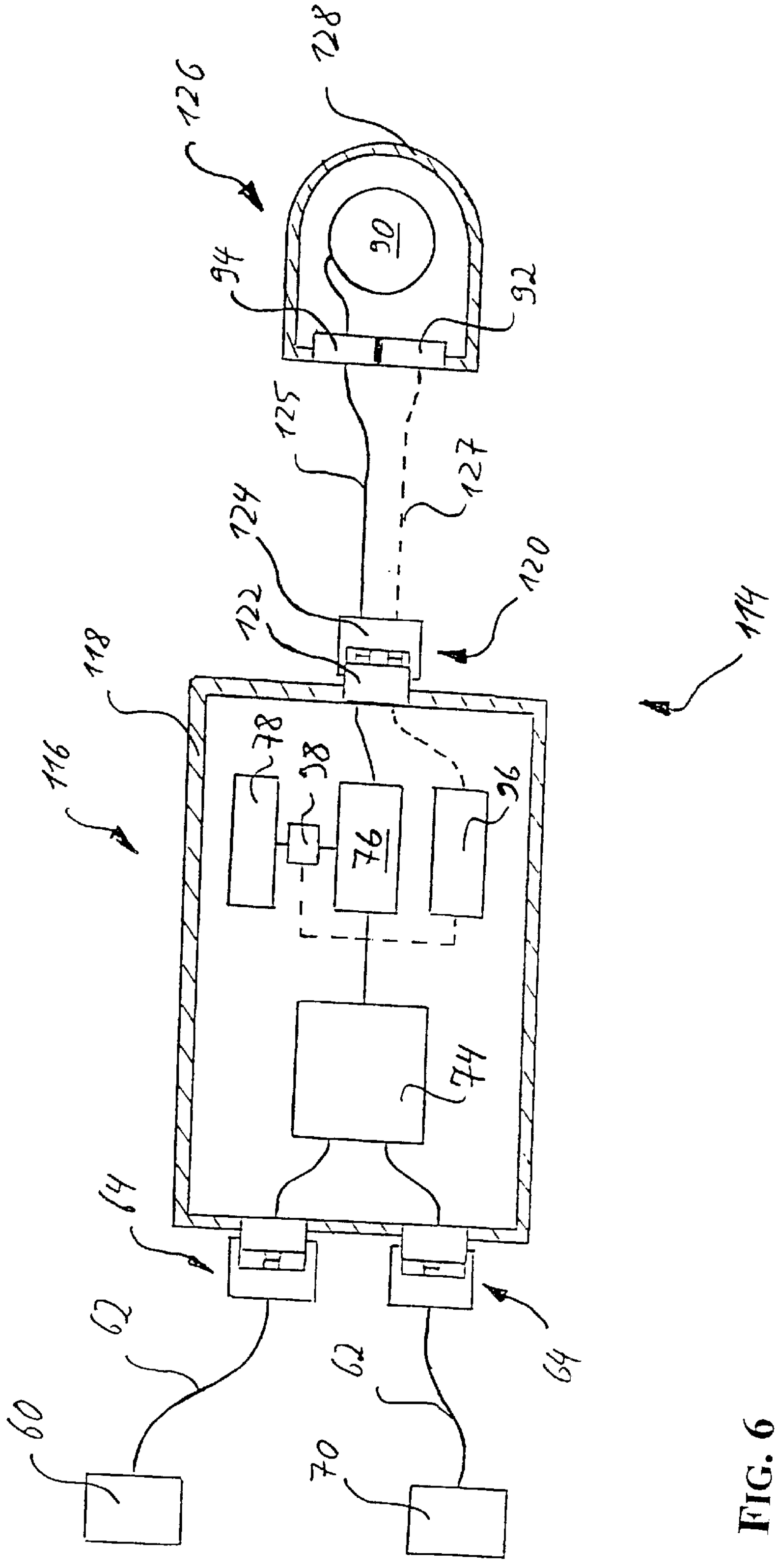
FIG. 6 is a schematic cross-sectional view of another embodiment of an implantable device, to which main module the power supply module is coupled via a flexible connecting lead.

A modified embodiment of an implantable device 114, as shown in FIG. 6, has a main module 116 with a main module housing 118 which holds the evaluation electronics 96 and the switching element 98 in addition to the components of the main module 56 already described in conjunction with FIG. 2. A power supply module 126 has a hermetically sealed outer housing which is made as a biocompatible protective housing 128 so that an additional outer housing can be dispensed with. A coupling element labeled 120 as a whole is used for electrical linkage of the power supply module 126 to the main module 116 and is divided into two parts which can be engaged in a hermetically sealed manner. A first of the two parts of the coupling element 120, a first half 122 is integrated into the main module housing 118 in a hermetically sealed manner, and the second half 124 is connected to the power supply module 126 via a flexible connecting lead. The connecting lead also comprises, in addition to a power line 125 for supplying power to the main module 116 and the secondary modules 60, 70 from the battery 90, a signal line 127 which allows the evaluation electronics 96 accommodated in the main module housing 118 to monitor the detector element 92.

Figure 7:
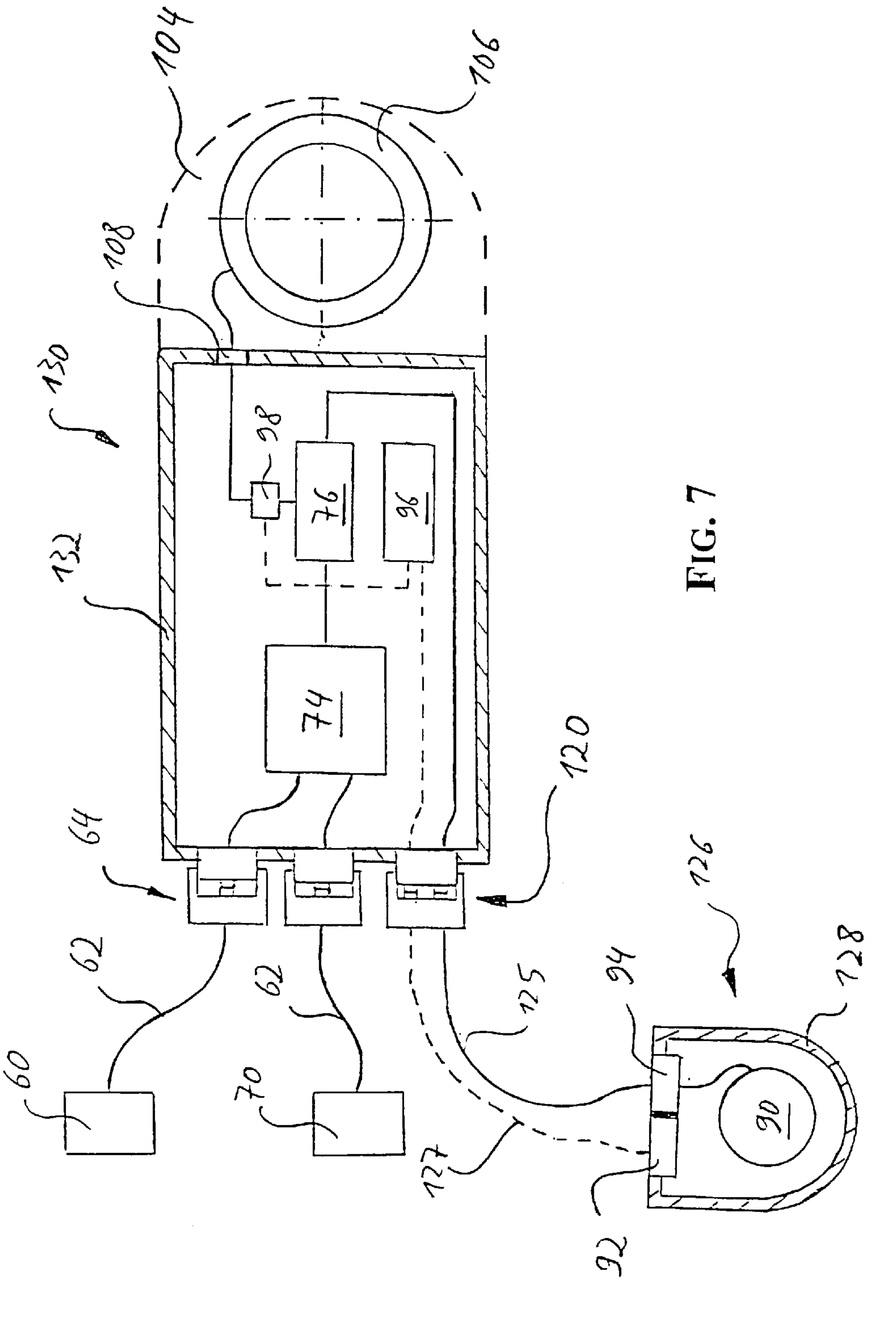
FIG. 7 is a schematic sectional view of another implantable device with flexibly coupled power supply module, the coil of the charging current feed arrangement being assigned to the main module and being accommodated in its own housing part.

The main module 130 of an implantable device as shown in FIG. 7 differs from the main module 116 of FIG. 6 essentially only in that the coil 106, as part of the charging current feed arrangement 78, is located outside of the main module housing 132 and is electrically connected to the switching element 98, via the through-hole 108, which is hermetically sealed, in a side wall of the main module housing. The coil 106 is potted with the biocompatible polymer 104 and is fixed on one side wall of the main module housing 132 which is perpendicular to a straight line which runs in the direction of the greatest extension of the main module housing 132. The coil 106 can form a unit with the main module housing 132 that is angled in at least one direction by the angle $\alpha$, as is the case in the outer housing 102 (see FIGS. 4 and 5). The first halves 66 of two coupling elements 64 are, in the same way as the first half 122 of the coupling element 120 in the main module housing 132, integrated into a side wall which is opposite the one to which the coil 106 is linked.

Figure 8:
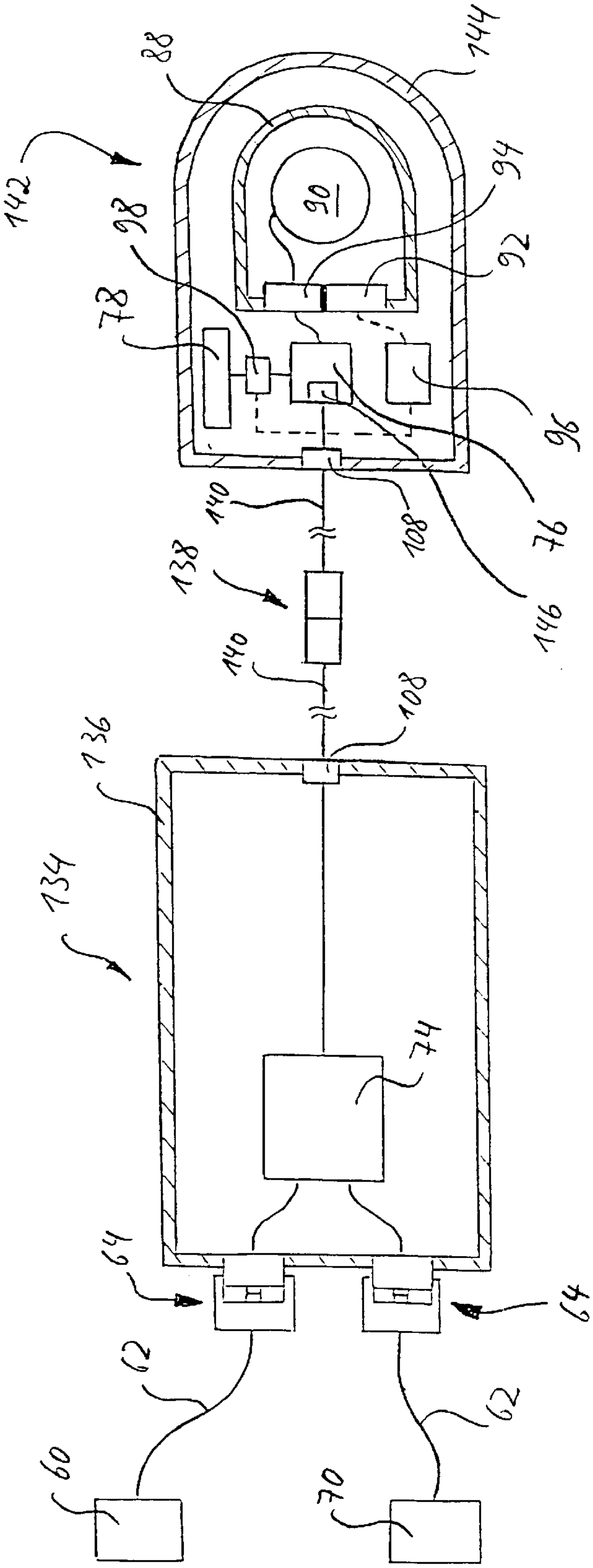
FIG. 8 is a view similar to that of FIG. 3, but with the power supply module supplying the main and secondary modules with power via a flexible connecting lead with a metallically separated coupling element.

FIG. 8 shows an implantable device which differs from that of FIG. 3 essentially only by the type of coupling of the power supply module 142 to the main module 134. This is achieved by means of a coupling element 138 which is made for a metallically separated and inductive connection. The coupling element 138 is preferably detachable and works according to the already described principle of power transmission between two coupling coils by resonant coupling, a principle known from German Patent DE 41 04 359 C2 and corresponding U.S. Pat. No. 5,279,292. The power stored in the battery 90 is converted by means of an oscillator 146 into an alternating oscillation, and is fed via the through-hole 108 in the outside wall of modified outer housing 144 and a flexible connecting lead 140 into a first coupling coil of the coupling element 138, by which, in the second coupling coil of the coupling element 138, an AC voltage is induced. The AC voltage is available via a second flexible connecting lead 140, a hermetically sealed through-hole 108 in the outside wall of the main module housing 136 and a rectifier (not shown) for operation of the signal processing electronics 74. It goes without saying that the power supply module 142 can also be modified in that the coil 106 of the power feed arrangement 78 can be located outside of the outer housing 144 and can be potted using a biocompatible polymer 104.

As follows from FIGS. 2, 6 and 7, the outer or protective housing of the power supply module comprises not only the detector element 92 and at least one switching element 94, but also at least the battery 90. However, it can be a good idea, especially in the outer housing, if this is provided in addition to the protective housing, to integrate other components which can be functionally assigned to the power supply module. These include, for example, the charging/discharging electronics 76, the charging current feed arrangement 78, the evaluation electronics 96 and additional switching elements 98. In this way, there results a preferably detachably coupled independent power supply module which is monitored itself and has protection functions which take effect in an unallowable operating state of the battery 90. The information about the unallowable operating state of the battery can be communicated to the implant wearer via warning means. If the implantable device is a hearing aid, the information can be fed directly into the signal path of the actuator component. Likewise, it can be transmitted via a transmitting coil into the charging device located outside of the body.

While various embodiments in accordance with the present invention have been shown and described, it is understood that the invention is not limited thereto, and is susceptible to numerous changes and modifications as known to those skilled in the art. Therefore, this invention is not limited to the details shown and described herein, and includes all such changes and modifications as are encompassed by the scope of the appended claims.

What is claimed is:

1. An implantable device comprising:

a power supply module; and a main module, said power supply module and said main module being interconnected by a coupling element;

wherein said power supply module includes a hermetically sealed protective enclosure;

a repeatedly rechargeable electrochemical battery for supplying electrical power via said coupling element to said main module, said repeatedly rechargeable electrochemical battery being housed within said enclosure;

a detector element fixed to said power supply module, and at least one switching element fixed to said power supply module and operatively connected to said detector element, said at least one switching element preventing at least one of recharging and discharging of said battery when said detector element detects that said battery is in an unallowable operating state.

2. The implantable device as claimed in claim 1, wherein said coupling element is designed to provide for a metallic contact between said power supply module and said main module.

3. The implantable device as claimed in claim 1, wherein said coupling element is designed to provide for an inductive coupling between said power supply module and said main module.

4. The implantable device as claimed in claim 1, wherein said coupling element is designed to provide for a detachable interconnection between said power supply module and said main module.

5. The implantable device as claimed in claim 4, wherein said coupling element is formed of two parts, a first part of which is assigned to the main module, and a second part which is assigned to the power supply module.

6. The implantable device as claimed in claim 5, wherein said first part of said coupling element is integrated into a housing of said main module.

7. The implantable device as claimed in claim 5, wherein said second part of said coupling element is integrated into said hermetically sealed protective enclosure.

8. The implantable device as claimed in claims 5, wherein said second part of said coupling element is integrated into said outer housing.

9. The implantable device as claimed in claim 5, wherein at least one of said first part and said second part of said coupling element is electrically connected to the associated module via a flexible connecting lead.

10. The implantable device as claimed in claim 1, wherein said hermetically sealed protective enclosure is biocompatible and defines an outer housing of said power supply module.

11. The implantable device as claim 10, wherein said hermetically sealed protective enclosure is biocompatible and defines an outer housing of said power supply module.

12. The implantable device as claimed in claim 1, wherein said power supply module further comprises a biocompatible outer housing, and said hermetically sealed protective enclosure is disposed within said outer housing.

13. The implantable device as claimed in claims 12, wherein said second part of said coupling element is integrated into said outer housing.

14. The implantable device as claimed in claim 1, wherein said main module comprises charging/discharging electronics for controlling at least one of recharging and discharging of the battery.

15. The implantable device as claimed in claim 1, further comprising a charging current feed arrangement into which power can be supplied via an external charging device, said charging device being separated from said power supply module and said main module.

16. The implantable device as claimed in claim 15, wherein said charging current feed arrangement is accommodated by a housing of said main module.

17. The implantable device as claimed in claim 15, wherein said charging current feed arrangement comprises a receiving coil which is fixed on an outer side of said main module.

18. The implantable device as claimed in claim 17, wherein said receiving coil is surrounded by a biocompatible polymer.

19. The implantable device as claimed in claim 17, wherein said receiving coil is made of a biocompatible metal.

20. The implantable device as claimed in claim 17, wherein said receiving coil is located on a longitudinal end of the housing of said main module, and wherein a straight line running in a direction of said main module forms an angle in a range from 5 to 25° with a line which is perpendicular to an axial direction of said receiving coil.

21. The implantable device as claimed in claim 17, wherein said receiving coil is affixed to said main module in a flexible manner by means of a biocompatible polymer which surrounds said receiving coil.

22. The implantable device as claimed in claim 1, further comprising evaluation electronics for monitoring said detector element; and wherein said least one switching element is electrically actuable by said evaluation electronics.

23. The implantable device as claimed in claim 22, wherein said main module comprises said evaluation electronics.

24. The implantable device as claimed in claim 1, wherein said coupling element further comprises means for transmitting an electrical signal in addition to said supplying of said electrical power.

25. The implantable device as claimed in claim 1, further comprising at least one secondary module which is connectable to said main module and which also is supplied with electric power by said power supply module.

26. A power supply module for an implantable device, said power supply module comprising:

a hermetically sealed protective enclosure;

a repeatedly rechargeable electrochemical battery for supplying electrical power via a coupling element to a main module of said implantable device, said battery being housed within said enclosure, and said coupling element being designed to provide for a detachable interconnection between said power supply module and said main module, a detector element fixed to said enclosure, and at least one switching element fixed to said enclosure and operatively connected to said detector element, said at least one switching element preventing at least one of recharging and discharging of said battery when said detector element detects that said battery is in an unallowable operating state.

27. The power supply module as claimed in claim 26, wherein said hermetically sealed protective enclosure is biocompatible and defines an outer housing of said power supply module.

28. The power supply module as claimed in claim 27, wherein a part of said coupling element associated to the power supply module is integrated into said hermetically sealed protective enclosure.

29. The power supply module as claimed in claim 26, wherein said power supply module further comprises a biocompatible outer housing, and said hermetically sealed protective enclosure is disposed within said outer housing.

30. The power supply module as claimed in claim 29, wherein a part of said coupling element associated to the power supply module is integrated into said outer housing.

31. The power supply module as claimed in claim 26, further comprising charging/discharging electronics for controlling at least one of recharging and discharging of the battery.

32. The power supply module as claimed in claim 26, further comprising a charging current feed arrangement into which power can be supplied via an external charging device.

33. The power supply module as claimed in claim 32, wherein said charging current feed arrangement comprises a receiving coil which is fixed on an outer side of the power supply module.

34. The power supply module as claimed in claim 33, wherein said receiving coil is surrounded by a biocompatible polymer.

35. The power supply module as claimed in claim 33, wherein said receiving coil is made of a biocompatible metal.

36. The power supply module as claimed in claim 33, wherein said receiving coil is located on a longitudinal end of a housing of said power supply module, and wherein a straight line running in a direction of the power supply module forms an angle in a range from 5 to 25° with a line which is perpendicular to an axial direction of said receiving coil.

37. The power supply module as claimed in claim 33, wherein said receiving coil is affixed to said power supply module in a flexible manner by means of a biocompatible polymer which surrounds said receiving coil.

38. The power supply module as claimed in claim 26, wherein said at least one switching element is integrated in said protective enclosure and is mechanically operable by said detector element in response to occurrence of said unallowable operating state of the battery.

39. The power supply module as claimed in claim 26, further comprising evaluation electronics for monitoring said detector element; and wherein said least one switching element is electrically actuable by said evaluation electronics.

* * * * *